(12) United States Patent
Machado et al.

(10) Patent No.: US 7,865,237 B2
(45) Date of Patent: Jan. 4, 2011

(54) METHODS AND SYSTEMS OF ACHIEVING HEMODYNAMIC CONTROL THROUGH NEUROMODULATION

(75) Inventors: Sandra Machado, Sao Paulo (BR); Ali Rezai, Bratenahl, OH (US); Andre Machado, Sao Paulo (BR)

(73) Assignee: The Cleveland Clinic Foundation, Cleveland, OH (US)

( * ) Notice: Subject to any disclaimer, the term of this patent is extended or adjusted under 35 U.S.C. 154(b) by 1013 days.

(21) Appl. No.: 11/222,773

(22) Filed: Sep. 12, 2005

(65) Prior Publication Data
US 2006/0100667 A1  May 11, 2006

(51) Int. Cl.
*A61N 1/372* (2006.01)
(52) U.S. Cl. .......................................................... 607/2
(58) Field of Classification Search ....................... 607/2
See application file for complete search history.

(56) References Cited

U.S. PATENT DOCUMENTS

| 4,776,349 | A |   | 10/1988 | Nashef et al. |       |
|-----------|---|---|---------|---------------|-------|
| 4,976,711 | A |   | 12/1990 | Parins et al. |       |
| 5,318,592 | A |   | 6/1994  | Schaldach     |       |
| 5,458,626 | A | * | 10/1995 | Krause ........................ | 607/50 |
| 5,707,400 | A |   | 1/1998  | Terry, Jr. et al. |   |
| 6,058,331 | A |   | 5/2000  | King          |       |
| 2003/0181958 | A1 |   | 9/2003 | Dobak, III   |       |
| 2003/0216792 | A1 | * | 11/2003 | Levin et al. ........................ | 607/48 |
| 2004/0019364 | A1 |   | 1/2004 | Kieval et al. |       |
| 2004/0030362 | A1 |   | 2/2004 | Hill et al.   |       |
| 2004/0049235 | A1 |   | 3/2004 | Deno et al.   |       |
| 2004/0210295 | A1 |   | 10/2004 | Brushey      |       |
| 2004/0230255 | A1 |   | 11/2004 | Dobak, III   |       |
| 2005/0197675 | A1 | * | 9/2005 | David et al. ........................ | 607/9 |
| 2007/0167984 | A1 | * | 7/2007 | Kieval et al. ........................ | 607/2 |

OTHER PUBLICATIONS

Netter, Frank H., Atlas of Human Anatomy, 2004, Icon Learning Systems, Third Edition, Plate 159.*
M. Cheatham et al., SHOCK: An Overview, Surgical Critical Care Service, Department of Surgical Education, Orlando Regional Medical Center, 5th edition; 2003; pp. 1-40, Orlando FL.
G. Brooksby et al., "Release of Blood from the Splanchnic Circulation in Dogs", Circulation Research, 1972:31, pp. 105-118, Dallas TX, vol. XXXI.
J. Carneiro et al, "Blood Reservoir Function of Dog Spleen, Liver and Intestine", American Journal of Physiology, 1977: 232(1) pp. H67-72.

(Continued)

*Primary Examiner*—Michael Kahelin
(74) *Attorney, Agent, or Firm*—Kenyon & Kenyon LLP

(57) ABSTRACT

Method of treating hemodynamic derangement and controlling the mobilization of splanchnic circulation. The method comprises applying a therapy signal to a celiac ganglion, a celiac plexus, a splanchnic nerve, or any combination thereof and adjusting the signal to effectuate treatment. The present invention also provides methods of treating hemodynamic derangement and controlling the mobilization of splanchnic circulation by transluminal modulation of the celiac ganglion, the celiac plexus, the splanchnic nerve.

15 Claims, 3 Drawing Sheets

OTHER PUBLICATIONS

G. A. Brooksby et al., "Dynamic Changes in Splanchnic Blood Flow and Blood Volume in Dogs During Activation of Sympathetic Nerves", Circulation Research, 1971, pp. 227-238, vol. XX1X.

International Search Report for PCT/US05/32769 filed Sep. 12, 2005.

J. L. Ardell et al., Differential sympathetic regulation of automatic, conductile, and contractile tissue in dog heart, American Physiological Society, Jun. 6, 1988, pp. H1050-H1059.

* cited by examiner

METHODS AND SYSTEMS OF ACHIEVING HEMODYNAMIC CONTROL THROUGH NEUROMODULATION

FIELD OF THE INVENTION

The present invention relates to methods and systems for treating hemodynamic derangement and methods and systems for controlling the mobilization of splanchnic circulation by electrically and/or chemically modulating a celiac ganglion, a celiac plexus, a splanchnic nerve, or any combination thereof.

BACKGROUND OF THE INVENTION

Diseases caused by or resulting in hemodynamic derangement, such as shock and congestive heart failure are widespread. The initial treatment for shock can include fluid resuscitation, and/or the administration of sympathomimetic and vasoactive drugs. Fluid resuscitation can involve the administration of protein containing (colloid) solutions or balanced salt (crystalloid) solutions. Such treatments, however, suffer from disadvantages. For example, crystalloids cause only a transient hemodynamic improvement and can cause pulmonary and peripheral edema. Colloids are expensive and can cause coagulopathy and decreased renal function. Moreover, in sepsis, there is an increase in microvascular permeability and minimal increases in hydrostatic pressure can produce clinically significant pulmonary edema. Vasoactive drugs currently used in shock treatment also cause a multitude of adverse effects including hypoperfusion to vital organs such as the kidneys, with potential organ damage and severe cardiac dysrhythmias and cardiac failure if preload exceeds contractile limits of the myocardium.

As such, a need exists for a method of selectively and locally treating hemodynamic derangement and otherwise achieving hemodynamic control without causing untoward systemic effects.

SUMMARY OF THE INVENTION

In an embodiment, the present invention provides a method of treating hemodynamic derangement comprising applying a therapy signal to a celiac plexus, a celiac ganglion, a splanchnic nerve or any combination thereof and adjusting the therapy signal to treat the hemodynamic derangement.

In another embodiment, the present invention provides a method of controlling the mobilization of splanchnic circulation comprising applying a therapy signal to a celiac plexus, a celiac ganglion, a splanchnic nerve or any combination thereof and adjusting the therapy signal to control the mobilization of the splanchnic circulation.

In another embodiment, the present invention provides a system for treating hemodynamic derangement comprising a therapy delivery device to apply a therapy signal to a celiac plexus, a celiac ganglion, a splanchnic nerve or any combination thereof. The system also includes a sensor to detect a hemodynamic parameter and generate a sensor signal. The system also includes a controller in communication with the therapy delivery device and the sensor to activate the therapy delivery device to initiate or adjust application of the therapy signal to the celiac plexus, celiac ganglion, splanchnic nerve or any combination thereof in response to the sensor signal to treat the hemodynamic derangement.

In another embodiment, the present invention provides a system for controlling the mobilization of splanchnic circulation comprising a therapy delivery device to apply a therapy signal to a celiac plexus, a celiac ganglion, a splanchnic nerve or any combination thereof. The system also includes a sensor to detect a hemodynamic parameter and generate a sensor signal. The system also includes a controller in communication with the therapy delivery device and the sensor to activate the therapy delivery device to initiate or adjust application of the therapy signal to the celiac plexus, celiac ganglion, splanchnic nerve or any combination thereof in response to the sensor signal to control the mobilization of the splanchnic circulation.

In any of the embodiments of the present invention the therapy delivery device can be an electrode, in which case the therapy signal is an electrical signal, or a drug port, in which case the therapy signal is a chemical signal.

DETAILED DESCRIPTION OF THE INVENTION

Figure 1:
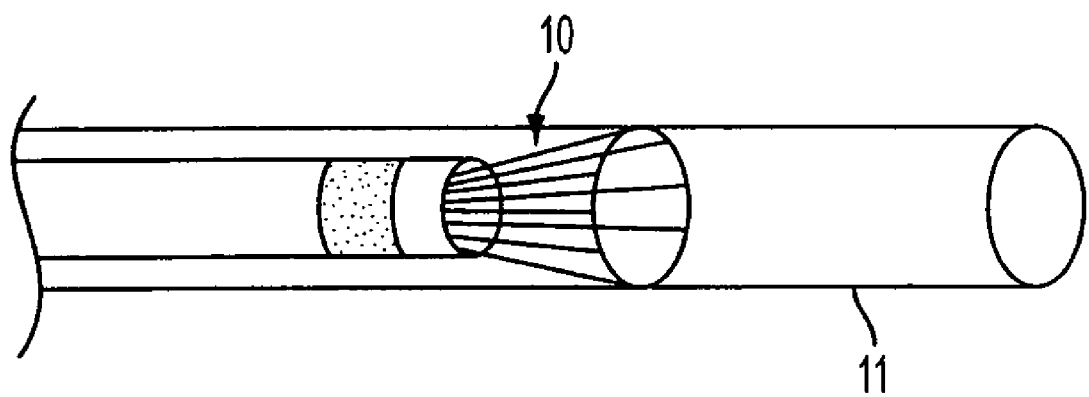
FIG. 1 is a therapy delivery device positioned within a lumen according to an embodiment of a method and system of the present invention.

In an embodiment, the present invention provides a method for treating hemodynamic derangement by neuromodulation of a celiac ganglion, a celiac plexus, a splanchnic nerve or any combination thereof. Hemodynamic derangement, according to the present invention, is an abnormality in the blood circulation volume caused either by reduction in the blood volume or increase of the vascular bed represented by changes in arterial blood pressure, central venous pressure, capillary pressures or any other kind of hemodynamic parameter. Such abnormalities include, for example, reduction in the effective circulating blood volume, reduction in venous return, vasoplegic vessels and/or reduction in cardiac output. Conditions resulting or caused by hemodynamic derangement include, for example, shock and congestive heart failure. Non-limiting examples of shock include septic, hemorrhagic or hypovolemic, cardiogenic, and neurogenic shock.

In another embodiment, the present invention provides a method for controlling mobilization of splanchnic circulation by neuromodulation of a celiac ganglion, a celiac plexus, a splanchnic nerve or any combination thereof. Splanchnic circulation is the circulation of blood of the splanchnic region vasculature, i.e. the vasculature that brings blood to and from the major abdominal organs including the liver, spleen, stomach, pancreas, large and small intestine. Exactly how the mobilization of the splanchnic circulation is controlled depends on the condition to be treated. For example, for septic or hemorrhagic shock, the mobilization of splanchnic circulation is controlled by increasing the mobilization of the splanchnic circulation into active circulation to increase an effective circulating volume of blood. For congestive heart failure, on the other hand, the mobilization of splanchnic blood circulation is controlled by decreasing the mobilization of the splanchnic circulation into active circulation to decrease the effective circulating volume of blood.

The neuromodulation of the present invention according to any of the methods of the present invention is accomplished by applying a therapy signal (i.e. an electrical and/or chemical signal) via a therapy delivery device (i.e. an electrode and/or drug port) to a celiac ganglion, a celiac plexus, a splanchnic nerve, or any combination thereof. The therapy signal can be applied to the left and/or right celiac ganglion and similarly, the therapy signal can be applied to a left and/or right splanchnic nerve. Although the therapy signal can be applied to the greater, lesser, or lowest thoracic splanchnic nerve, preferably, the splanchnic nerve to which the therapy signal is applied is the greater or the lesser splanchnic nerve.

The therapy delivery device can be placed or implanted in contact with or in communication with any of the aforementioned sites. For example, the therapy delivery device may directly contact the celiac ganglion, celiac plexus, or splanchnic nerve or the therapy delivery device may be placed in a lumen or vessel adjacent to the celiac ganglion, celiac plexus, or splanchnic nerve. As such, several routes and methods of implantation are possible in order to reach the celiac ganglion, celiac plexus, or splanchnic nerve with a therapy delivery device. Such routes of implantation include intraluminal, including intravascular such as intravascular venous and intravascular arterial. The therapy delivery devices can be delivered endoscopically, percutaneously, or laparoscopically. More invasive alternatives to implant the electrode(s) are possible under direct visualization through open surgeries such as laparotomy, for example. In a preferred embodiment, the therapy delivery device is placed in the inferior vena cava at the level of the celiac ganglion, celiac plexus or splanchnic nerve.

With respect to the intravascular route, an exemplary method of reaching the desired target site is as follows: With the patient's leg slightly abducted, the femoral artery 3-4 centimeters below the inguinal ligament is located. The femoral vein is located just medial and parallel to the femoral artery. The electrode (carried within a needle for example) is inserted into the femoral vein at a 30-45° angle via the Seldinger technique. The therapy delivery device is passed through the femoral vein, through the iliac vein through the inferior vena cava to the level of the celiac ganglion, celiac plexus, or splanchnic nerve. Once at the appropriate level, x-ray or fluoroscopy guidance can be used to optimally position the therapy delivery device. The therapy delivery device can also be activated to help further define the optimal position (i.e. by recording the acute changes in hemodynamic parameters at different electrical settings such as different voltages, rates, pulse widths, pulse morphologies, etc).

In a preferred embodiment, the neuromodulation according to the methods of the present invention is performed acutely for a short period of time, such as less than ten days until the patient's hemodynamic state is returned to normal. As such, in this preferred embodiment, the therapy delivery device is only placed temporarily in the patient.

An open-loop or closed-loop feedback mechanism may be used in conjunction with any of the methods of the present invention. In an open-looped feedback mechanism, a professional can monitor hemodynamic parameters of the patient and adjust accordingly the therapy signal applied to the celiac ganglion, the celiac plexus, the splanchnic nerve or any combination thereof. Non-limiting examples of hemodynamic parameters that can be monitored include arterial blood pressure, central venous pressure, capillary pressure, systolic pressure variation, arterial blood gases, cardiac output, systemic vascular resistance, pulmonary artery wedge pressure, and mixed venous oxygen saturation. Other parameters such as body temperature and respiratory rate can also be monitored and processed as part of the feedback mechanism. In a closed-loop feedback mechanism, the hemodynamic parameters are processed by a sensor(s) and the neuromodulation is continuously adjusted according to the output generated by the sensor(s). Specifically, a sensor(s) detects a hemodynamic parameter and generates a sensor signal. The sensor signal is processed by a sensor signal processor that provides a control signal to a signal generator. The signal generator, in turn, generates a response to the control signal by activating or adjusting the therapy signal applied by the therapy delivery device to the celiac ganglion, the celiac plexus, the splanchnic nerve or any combination thereof. The control signal may be an indication to initiate, terminate, increase, decrease or change the rate or pattern of a pulsing parameter of the neuromodulation and the response to the control signal can be the respective initiation, termination, increase, decrease or change in rate or pattern of the respective pulsing parameter. The processing of closed-loop feedback systems for electrical neuromodulation is described in more detail in respective U.S. Pat. Nos. 6,058,331 and 5,711,316, both of which are incorporated by reference herein.

The present invention also provides a system for treating hemodynamic derangement or controlling the mobilization of splanchnic circulation. Specifically, in such embodiments, the system comprises a therapy delivery device to apply a therapy signal (which can be an electrical signal and/or a chemical signal) to a celiac plexus, a celiac ganglion, a splanchnic nerve or any combination thereof. The system also includes a sensor to detect a hemodynamic parameter and generate a sensor signal. Non-limiting examples of hemodynamic parameters include blood pressure, pulse rate, arterial blood gases, cardiac output, systemic vascular resistance, pulmonary artery wedge pressure, and mixed venous oxygen saturation. The system also includes a controller in communication with the therapy delivery device and the sensor to process the sensor signal and activate the therapy delivery device to initiate or adjust application of the therapy signal to the celiac plexus, celiac ganglion, splanchnic nerve, or any combination thereof in response to the sensor signal to treat the hemodynamic derangement or control the mobilization of the splanchnic circulation. The therapy delivery device then applies the therapy signal to the celiac plexus, celiac ganglion, splanchnic nerve, or any combination thereof.

In embodiments where the therapy delivery device is an electrode and the therapy signal is an electrical signal, activating the electrode to initiate or adjust application of the electrical signal includes terminating, increasing, decreasing, or changing the rate or pattern of a pulsing parameter of the electrical stimulation and the electrical signal can be the respective termination, increase, decrease, or change in the rate or pattern of the respective pulsing parameter.

In embodiments where the therapy delivery device is a drug port and the therapy signal is a chemical signal, activating the drug port to initiate or adjust application of the chemical signal can be an indication to terminate, increase, decrease or change the rate or pattern of the amount or type of chemical agent administered, and the chemical signal can be the respective initiation, termination, increase, decrease, or change in the rate or pattern of the amount or type of chemical agent administered.

FIG. 1 provides an illustration of a therapy delivery device 10 that can be used in accordance with an embodiment of a system of the present invention, which has been inserted into a blood vessel 11 at a position adjacent a celiac ganglion. Therapy delivery device 10 is connected via a stimulation lead/catheter (in embodiments where therapy delivery device is an electrode and drug port respectively) to a controller (not shown). The therapy delivery device may be placed permanently or temporarily on or adjacent to the celiac plexus, celiac ganglion, or splanchnic nerve.

The controller of an embodiment of a system of the present invention is used to operate and supply power to the therapy delivery device and enable the therapy delivery device to deliver a therapy signal (such as an electrical and/or chemical signal) to the celiac plexus, celiac ganglion, splanchnic nerve or any combination thereof. The controller may be powered by a battery (which can be rechargeable), an external power supply, a fuel cell, or a battery pack for external use. The controller may also be integral with the therapy delivery device (such as a single stimulation lead/power generator). When the therapy delivery device is an electrode, the controller may change the output to the electrode by way of polarity, pulse width, amplitude, frequency, voltage, current, intensity, duration, wavelength, and/or waveform. When the therapy delivery device is a drug port, the controller may change its output such that a pump, pressure source, or proportionally controlled orifice increases or decreases the rate at which the pharmaceutical is delivered to the target site. The controller may operate any number or combination of electrodes and drug ports. For example, the controller may be connected to stimulation leads and a peristaltic pump for delivering a pharmaceutical to the target site near the stimulation leads. The controller may be implanted within the patient or it may be positioned by leads outside of the patient. A portion of the control system may be external to the patient's body for use by the attending physician to program the implanted controller and to monitor its performance. This external portion may include a programming wand which communicates with the implanted controller by means of telemetry via an internal antenna to transmit parameter values (as may be selectively changed from time to time by subsequent programming) selected at the programmer unit, such as a computer. The programming wand also accepts telemetry data from the controller to monitor the performance of the therapy delivery device.

In embodiments where the controller enables an electrode to deliver an electrical signal to a celiac ganglion, celiac plexus, splanchnic nerve, or any combination thereof, the electrical signal may be episodic, continuous, phasic, in clusters, intermittent, upon demand by the patient or medical personnel, or preprogrammed to respond to a sensor. Preferably, the oscillating electrical signal is operated at a voltage between about 0.1 microvolts to about 20 V. More preferably, the oscillating electrical signal is operated at a voltage between about 1 V to about 15 V. For microstimulation, it is preferable to stimulate within the range of 0.1 microvolts to about 1 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the electrode is monopolar; bipolar when the electrode is bipolar; and multipolar when the electrode is multipolar. The waveform may be, for example, biphasic, square wave, sine wave, or other electrically safe and feasible combinations. The electrical signal may be applied to multiple target sites simultaneously or sequentially.

In embodiments where the controller enables a drug port to deliver a chemical signal to a celiac ganglion, celiac plexus, splanchnic nerve, or any combination thereof, a chemical agent may be delivered prior to, concurrent with, subsequent to or instead of electrical neuromodulation. The chemical agent may be a neurotransmitter mimic; neuropeptide; hormone; pro-hormone; antagonist, agonist, reuptake inhibitor, or degrading enzyme thereof; peptide; protein; therapeutic agent; amino acid; nucleic acid; stem cell or any combination thereof and may be delivered by a slow release matrix or drug pump. The delivery of the chemical agent may be continuous, intermittent, chronic, phasic, or episodic. The chemical agents preferably work on one or more of the receptor sites of the autonomic nervous system such as the adrenergic receptors, cholinergic receptors (nicotinic and muscarinic), purinergic, and nitric oxide receptors. Non-limiting examples of chemical agents include, prazosin, yohimbine, atelenol, sulbutamol, and atropine.

Figure 2:
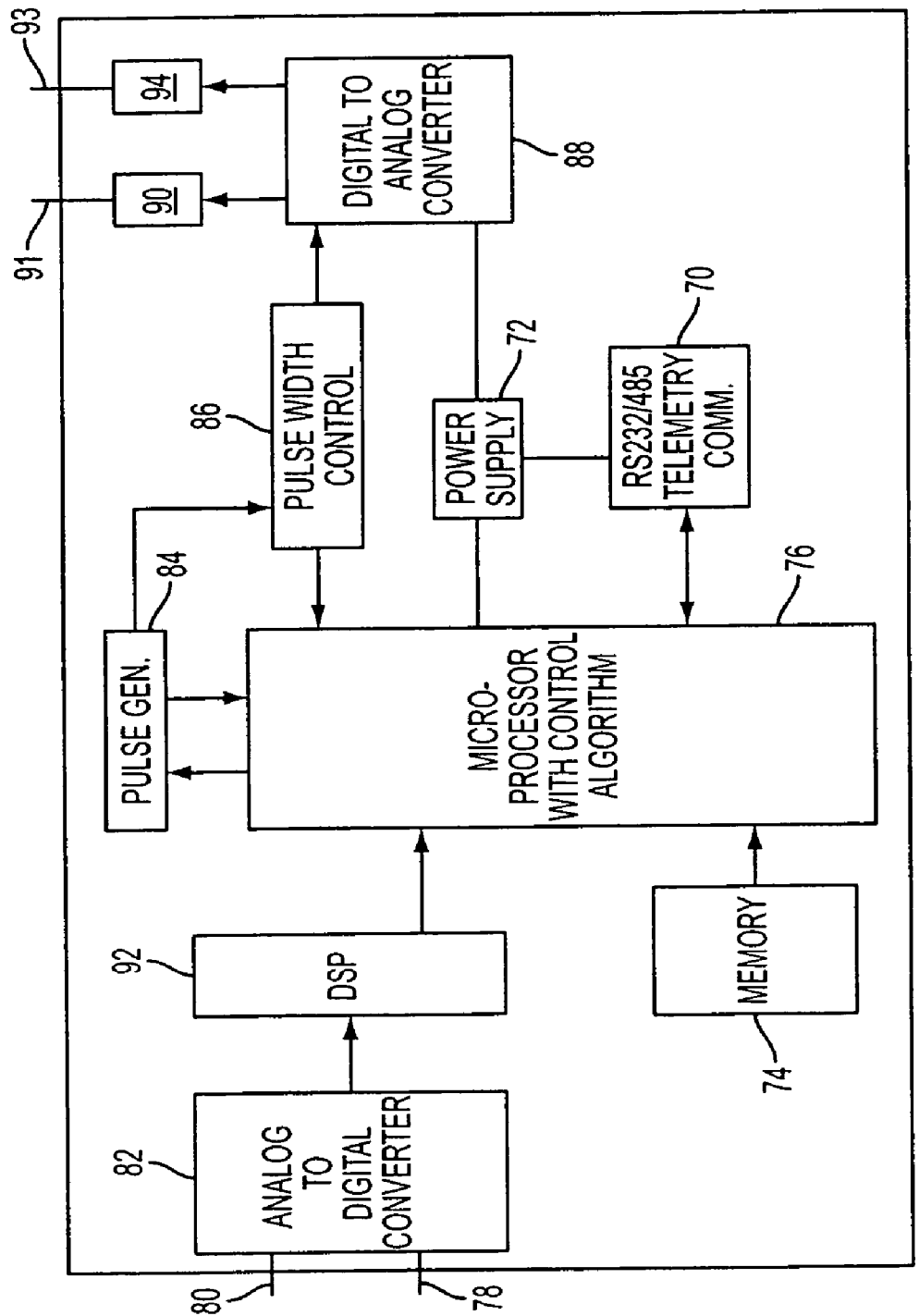
FIG. 2 is a schematic illustration of the components used in a controller of an embodiment of a system of the present invention.

Closed-loop electrical stimulation, according to the present invention can be achieved by a modified form of an implantable SOLETRA, KINETRA, RESTORE, or SYNERGY signal generator available from Medtronic, Minneapolis, Minn. as disclosed in U.S. Pat. No. 6,353,762, the teaching of which is incorporated herein in its entirety, a controller as described in FIG. 2, or utilization of CIO DAS 08 and CIO-DAC 16 I processing boards and an IBM compatible computer available from Measurement Computing, Middleboro, Mass. with Visual Basic software for programming of algorithms. With reference to FIG. 2, an illustration of a non-limiting example of a controller comprising a microprocessor 76 such as an MSP430 microprocessor from Texas Instruments Technology, analog to digital converter 82 such as AD7714 from Analog Devices Corp., pulse generator 84 such as CD1877 from Harris Corporation, pulse width control 86, lead driver drivers 90 and 94, digital to analog converter 88 such as MAX538 from Maxim Corporation, power supply 72, memory 74, and communications port or telemetry chip 70 are shown. Optionally, a digital signal processor 92 is used for signal conditioning and filtering. Input leads 78 and 80 and output lead to lead (therapy delivery device) 91 and drug delivery device (therapy delivery device) 93 are also illustrated. Additional stimulation leads, sensors, and therapy delivery devices may be added to the controller as required. As a non-limiting example, inputs from sensors, such as a pulmonary artery wedge pressure sensor, are input to analog to digital converter 82. Microprocessor 76 receiving the sensor inputs uses algorithms to analyze the hematological parameter of the patient and using PID, Fuzzy logic, or other algorithms, computes an output to pulse generator and/or drug delivery device drivers 90 and 94, respectively, to neuromodulate the target site where the therapy delivery devices are placed. The output of analog to digital converter 82 is connected to microprocessor 76 through a peripheral bus including address, data and control lines. Microprocessor 76 processes the sensor data in different ways depending on the type of transducer in use. When the signal on the sensor indicates a hemodynamic parameter outside of threshold values, for example reduced pulmonary artery wedge pressure, programmed by the clinician and stored in a memory, the electrical signal applied through output drivers 90 and 94 of the controller will be adjusted. The output voltage or current from the controller are then generated in an appropriately configured form (voltage, current, frequency), and applied to the one or more therapy delivery devices placed at the target site for a prescribed time period to elevate the pulmonary artery wedge pressure. If the patient's pulmonary artery wedge pressure as monitored by the system is not outside of the normal threshold limits, or if the controller output (after it has timed out) has resulted in a correction of the pulmonary artery wedge pressure to within a predetermined threshold range, no further therapy signal is applied to the target site and the controller continues to monitor the patient via the sensors.

Figure 3:
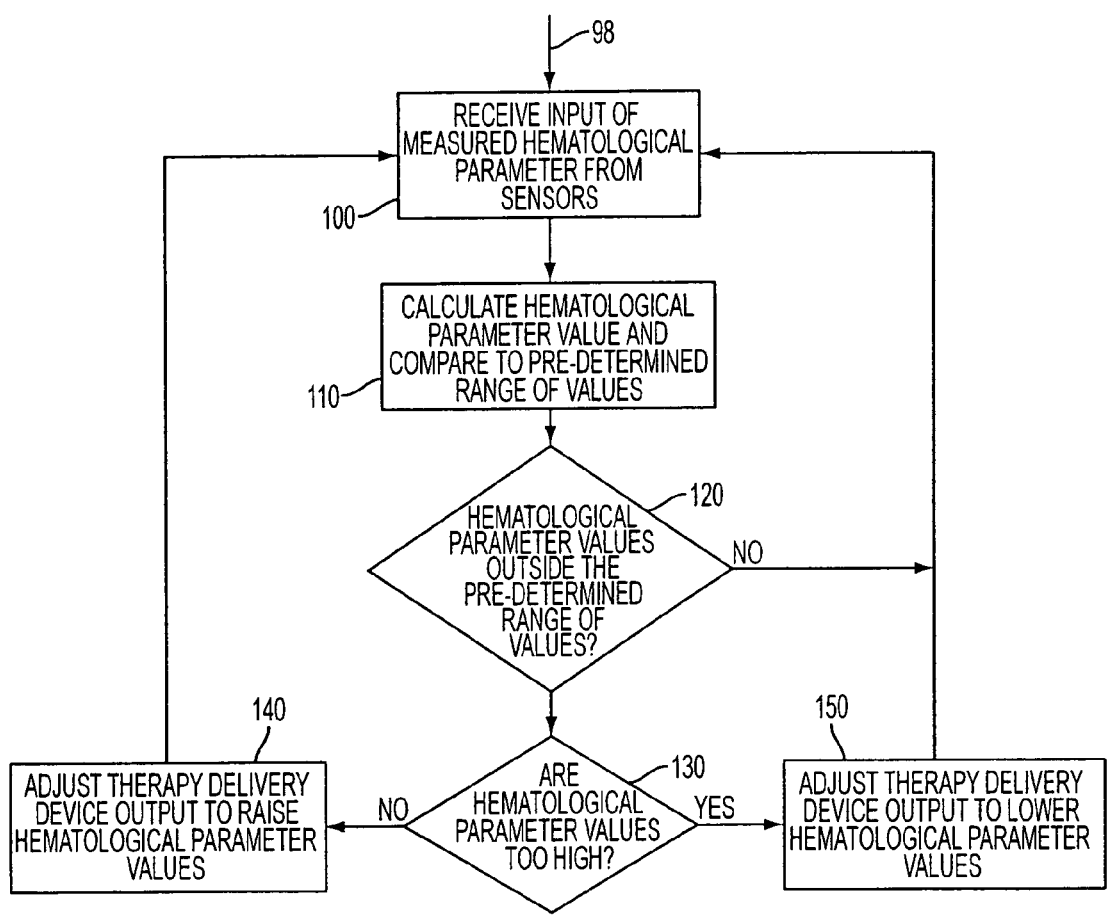
FIG. 3 is a block diagram of an algorithm to determine action taken by a controller microprocessor in response to sensor input according to an embodiment of a system of the present invention.

A block diagram of an algorithm which may be used in the present invention is shown in FIG. 3.

Referring to FIG. 3, suitably conditioned and converted sensor data 98 is input to the algorithm in block 100. The program computes at least one value of at least one hemodynamic parameter such as, for example pulmonary artery wedge pressure or cardiac output, and compares the measured value of the hemodynamic parameter to a pre-determined range of values, which is determined in advance to be the desired therapeutic range of values. This range is programmed into the microprocessor via the telemetry or communications port of the controller. The algorithm compares 110, and then determines whether or not the measured value lies outside the pre-determined range of values 120. If the measured hemodynamic parameter value is not outside the pre-determined range of values, the program continues to monitor the sensors and reiterates the comparison part of the algorithm. If the measured hemodynamic parameter value is outside of the pre-determined range of values, a determination or comparison is made 130, as to whether the value is too high or too low compared with the pre-determined range. If the hemodynamic parameter value is too high, an adjustment to the therapy delivery device is made 150, to lower the hemodynamic parameter value of the patient by calculating an output signal for pulse generator or drug delivery device to deliver a sufficient amount of the pharmaceutical or electrical stimulation to lower the hemodynamic parameter of the patient. The algorithm continues to monitor the hemodynamic parameter following the adjustment. If the hemodynamic parameter value is too low then an adjustment to the therapy delivery device is made 140, to raise the hemodynamic parameter value by calculating an output signal for the pulse generator or drug delivery device to deliver a sufficient amount of a pharmaceutical or electrical stimulation to raise the hemodynamic parameter value of the patient. The algorithm continues to monitor the hemodynamic parameter of the patient 100, following the adjustment. The amount of adjustment made may be determined by proportional integral derivative algorithms of by implementation or Fuzzy logic rules.

With respect to the control of specific electrical parameters, the stimulus pulse frequency may be controlled by programming a value to a programmable frequency generator using the bus of the controller. The programmable frequency generator provides an interrupt signal to the microprocessor through an interrupt line when each stimulus pulse is to be generated. The frequency generator may be implemented by model CDP1878 sold by Harris Corporation. The amplitude for each stimulus pulse may be programmed to a digital to analog converter using the controller's bus. The analog output is conveyed through a conductor to an output driver circuit to control stimulus amplitude. The microprocessor of the controller may also program a pulse width control module using the bus. The pulse width control provides an enabling pulse of duration equal to the pulse width via a conductor. Pulses with the selected characteristics are then delivered from signal generator through a cable and lead to the target site or to a device such as a proportional valve or pump. The microprocessor executes an algorithm to provide stimulation with closed loop feedback control as shown in U.S. Pat. No. 5,792, 186 which is incorporated herein by reference in its entirety. For some types of sensors, a microprocessor and analog to digital converter will not be necessary. The output from sensor can be filtered by an appropriate electronic filter in order to provide a control signal for signal generator. An example of such a filter is found in U.S. Pat. No. 5,259,387 "Muscle Artifact Filter," issued to Victor de Pinto on Nov. 9, 1993, incorporated herein by reference in its entirety.

At the time the therapy delivery device is positioned, the clinician programs certain key parameters into the memory of the implanted device via telemetry. These parameters may be updated subsequently as needed. The clinician may also program the the range of values for pulse width, amplitude and frequency which the therapy delivery device may use to optimize the therapy. The clinician may also choose the order in which the parameter changes are made. Alternatively, the clinician may elect to use default values or the microprocessor may be programmed to use fuzzy logic rules and algorithms to determine output from the therapy delivery device to the patient based on sensor data and threshold values for the hematological parameter.

The foregoing description has been set forth merely to illustrate the invention and is not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. A method of treating congestive heart failure in a patient in need thereof comprising:
    inserting an electrode into a lumen of the body of a patient suffering from congestive heart failure;
    advancing the electrode to a point in the lumen wherein the electrode is in electrical communication with a celiac plexus, a celiac ganglion or a splanchnic nerve; and
    applying an electrical signal to the celiac plexus, celiac ganglion or splanchnic nerve,
    wherein applying the electrical signal decreases the mobilization of the splanchnic circulation into active circulation to decrease the effective circulating volume of blood of the patient.

2. The method of claim 1, wherein the electrical signal is applied to the celiac ganglion.

3. The method of claim 2, wherein the electrical signal is applied to a left celiac ganglion, a right celiac ganglion, or both.

4. The method of claim 1, wherein the electrical signal is applied to the splanchnic nerve.

5. The method of claim 4, wherein the electrical signal is applied to the greater splanchnic nerve, the lesser splanchnic nerve, the lowest thoracic splanchnic nerve, or any combination thereof.

6. The method of claim 4, wherein the electrical signal is applied to a left splanchnic nerve, a right splanchnic nerve, or both.

7. The method of claim 1, wherein the electrical signal is applied to the celiac plexus, the celiac ganglion, the splanchnic nerve or any combination thereof for a period of less than ten days.

8. The method of claim 1, wherein the electrical signal is applied to the celiac plexus.

9. The method of claim 1, wherein the electrical signal has a voltage range of 0.1 μV to about 20 V and a frequency range of about 2 Hz to about 2500 Hz.

10. The method of claim 9, further comprising:
adjusting the electrical signal to control the mobilization of splanchnic circulation.

11. The method of claim 1 further comprising:
sensing a hematological parameter associated with the splanchnic circulation and generating a sensor signal; and
adjusting the electrical signal in response to the sensor signal to control the mobilization of the splanchnic circulation.

12. The method of claim 1, wherein the lumen is a blood vessel.

13. The method of claim 12, wherein the blood vessel is an artery.

14. The method of claim 12, wherein the blood vessel is a vein.

15. The method of claim 14, wherein the vein is the inferior vena cava.

* * * * *